(12) United States Patent
Ren et al.

(10) Patent No.: US 9,970,909 B2
(45) Date of Patent: May 15, 2018

(54) DEVICE AND METHOD FOR EVALUATING SCALE INHIBITOR

(71) Applicant: Nanjing University, Nanjing (CN)

(72) Inventors: Hongqiang Ren, Nanjing (CN); Zhanhui Shen, Nanjing (CN); Ke Xu, Nanjing (CN); Jinju Geng, Nanjing (CN); Xinkun Ren, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 1282 days.

(21) Appl. No.: 13/905,168

(22) Filed: May 30, 2013

(65) Prior Publication Data

US 2013/0325361 A1    Dec. 5, 2013

(30) Foreign Application Priority Data

Jun. 1, 2012    (CN) .......................... 2012 1 0178531

(51) Int. Cl.
*G01N 31/00* (2006.01)
*G01N 33/00* (2006.01)
*G01N 31/16* (2006.01)
*B01L 3/08* (2006.01)

(52) U.S. Cl.
CPC ............. *G01N 33/00* (2013.01); *G01N 31/16* (2013.01); *B01L 3/08* (2013.01)

(58) Field of Classification Search
CPC ........ B65D 23/04; G01N 33/00; G01N 31/16; B01L 3/08

USPC .......................................................... 702/22
See application file for complete search history.

(56) References Cited

U.S. PATENT DOCUMENTS

2004/0141909 A1* 7/2004 Christensen .......... C01B 17/806
                                                                 423/523
2008/0237042 A1* 10/2008 Feng ...................... G01N 27/36
                                                                 204/412

OTHER PUBLICATIONS

Mo, Jian-song., Oxidation inhibition of sulfite in dual alkali flue gas desulfurization system., Journal of Environmental Sciences 19(2007) 226-231.*
Sigma-Aldrich., MultiNeckFlasks Sigma Aldrich Glassware Catalog., Jun. 16, 2009.*

* cited by examiner

*Primary Examiner* — Yoshihisa Ishizuka
(74) *Attorney, Agent, or Firm* — Matthias Scholl, PC; Matthias Scholl

(57) ABSTRACT

A device for evaluating a scale inhibitor for a circulating cooling water system, the device including: an open vessel, the open vessel including a first fixing hole, a second fixing hole, and at least one test hole; a stirrer; a test piece; a condenser; and a constant temperature heater. The open vessel is disposed inside the constant temperature heater. The first fixing hole is used to fix the stirrer. The second fixing hole is used to fix the condenser. The test hole is used to fix the test piece.

4 Claims, 2 Drawing Sheets

DEVICE AND METHOD FOR EVALUATING SCALE INHIBITOR

CROSS-REFERENCE TO RELATED APPLICATIONS

Pursuant to 35 U.S.C. § 119 and the Paris Convention Treaty, this application claims the benefit of Chinese Patent Application No. 201210178531.0 filed Jun. 1, 2012, the contents of which are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

Field of the Invention

The invention relates to the evaluation of a scale inhibitor, and more particularly to a device and a method for evaluating a scale inhibitor for a circulating cooling water system.

Description of the Related Art

Typical methods for evaluating a scale inhibitor include a static method and a dynamic method.

The static method for evaluating a scale inhibitor includes a deposition method, a bubbling method, a nephelometry method, a critical pH method, a pH displacement method, and a conductance method. A typical method of calcium carbonate deposition includes: preparing a mixed solution including calcium ions, bicarbonate ions, and a scale inhibitor; heating the mixed solution to form scale; measuring calcium ions remained in the mixed solution to evaluate the performance of the scale inhibitor. The higher the calcium ion concentration remains in the mixed solution, the better performance of the scale inhibitor is. The bubbling method includes pumping the air into a prepared test solution for accelerating scale formation, and evaluating the performance of a scale inhibitor by measuring a stable calcium ion concentration of the test solution. A Glass electrode method, the nephelometry method, the conductance method, the pH displacement method, and the critical pH method are capable of reflecting the chelation of the scale inhibitor and the capability of stabilizing calcium ions, but are not capable of reflecting dispersion and lattice distortion of the scale inhibitor. However, in practical working condition of the circulating cooling water system, the scale formation includes crystallization of free calcium ions into calcium carbonate, attachment of the calcium carbonate crystal on a device surface, and a growth period of the calcium carbonate crystal; and the scale formation cannot be reflected by the static methods for evaluating scale inhibitors. In contrast, the dynamic method can effectively reflect the scale formation in the presence of the scale inhibitor.

The dynamic method is to simulate working conditions of practical production in the laboratory, including flow rate, flow pattern, temperature, water, metal material, and heat transfer intensity. The dynamic method is an ideal neutralizing test method. However, the dynamic method is complicate and time consuming (usually longer than ten days); besides, the adapted device is complicated and expensive.

A typical method for evaluating an antiosmosis scale inhibitor includes establishing a dynamic circulating system, adding scale-forming ion solution to the system at intervals, recording parameters during the operation of the system, and evaluating the performance of the scale inhibitor. The method is only applicable to antiosmosis systems, but not able to reflect the condition in circulating cooling water system.

SUMMARY OF THE INVENTION

In view of the above-described problems, it is one objective of the invention to provide a device and a method for evaluating a scale inhibitor for a circulating cooling water system. The invention employs an electronic stirrer to produce a water flow through a surface of a metal test piece, and heat at a constant temperature to imitate a working condition of the circulating cooling water. The invention evaluates the performance of the scale inhibitor by measuring a stable calcium ion concentration in the test solution and an increased weight of the test piece. The method of the invention properly combines advantages of the conventional static method and the dynamic method, effectively reflects the chelation, as well as the dispersion and the lattice distortion ability of the scale inhibitor.

To achieve the above objective, in accordance with one embodiment of the invention, there is provided a device for evaluating a scale inhibitor for a circulating cooling water system, the device comprising: an open vessel, the open vessel comprising a first fixing hole, a second fixing hole, and at least one test hole; a stirrer; a test piece; a condenser; and a constant temperature heater. The open vessel is disposed inside the constant temperature heater. The first fixing hole is used to fix the stirrer. The second fixing hole is used to fix the condenser. The test hole is used to fix the test piece.

In a class of this embodiment, the open vessel is provided with a first test hole, a second test hole, and a third test hole. The first test hole, the second test hole, the third test hole, and the second fixing hole are evenly arranged around the first fixing hole.

In a class of this embodiment, the condenser is a glass tube comprising two ends. One end of the glass tube communicates with the air inside the open vessel; and the other end of the glass tube communicates with the atmosphere. The glass tube has an outer diameter between 3 and 6 mm and a length between 30 and 40 cm for condensing the water vapor.

In a class of this embodiment, the test piece is a stainless steel test piece. The stainless steel test piece is suspended in a test solution in the open vessel. An arrangement of the stainless steel test piece is in parallel with a flow direction of the test solution.

In accordance with another embodiment of the invention, there is provided a method for evaluating a scale inhibitor for a circulating cooling water system. The method comprises the following steps:

1) treatment of a test piece:
   washing the test piece in acetone in the presence of ultrasonic wave, desiccating the test piece in a desiccator;
2) preparation of a test solution:
   a) preparing a 0.01 mol/L EDTA standard solution, a 200 g/L potassium hydroxide solution, and a 0.01 mol/L borax buffer solution, respectively;
   b) preparing a sodium bicarbonate mother solution and a calcium chloride mother solution; and titrating the sodium bicarbonate mother solution and the calcium chloride mother solution by using a hydrochloric acid standard solution and the EDTA standard solution, respectively; and c) adding distilled water into a volumetric flask; adding the calcium chloride mother solution, a scale inhibitor solution, the borax buffer solution, and the sodium bicarbonate mother solution into the volumetric flask, respectively; and finally adding distilled water to a constant volume of the volumetric flask to yield the test solution having a calcium ion concentration of 240 mg/L and a bicarbonate ion concentration of 366 mg/L;

3) scale formation test:

transferring the test solution prepared in step 2) to an open vessel; providing three test pieces prepared in step 1) and measuring a weight thereof represented by $m_{11}$, $m_{12}$, and $m_{13}$, respectively; fixing the three test pieces in a first test hole, a second test hole, and a third test hole by using stainless steel strips, respectively, for suspending the three test pieces in the test solution; fixing a condenser in a second fixing hole; fixing a stirrer in a first fixing hole, controlling a stirrer speed between 100 and 300 rpm; maintaining the open vessel inside a constant temperature heater for 10 h; and taking off the three test pieces, desiccating, and measuring weight thereof represented by $m_{11}'$, $m_{12}'$, $m_{13}'$, respectively;

4) measurement of calcium ion concentration:

cooling the test solution in the open vessel to a room temperature, transferring and filtering the test solution for collecting a filtrate by using an Erlenmeyer flask; adding distilled water, the potassium hydroxide solution prepared in step 2), and calconcarboxylic acid into the Erlenmeyer flask to yield a mixture; titrating the mixture in parallel for three times by using the EDTA standard solution obtained in step 2); and calculating calcium ion concentration represented by $\rho_{11}$, $\rho_{12}$, and $\rho_{13}$, respectively;

5) blank test:

repeating steps 1)-4) to conduct the blank test: preparing a test solution without adding the scale inhibitor; measuring weight of three test pieces before the blank test represented by $m_{01}$, $m_{02}$, and $m_{03}$; measuring weight of the three test pieces after the blank test represented by $m_{01}'$, $m_{02}'$, and $m_{03}'$; titrating calcium ion concentration of the test solution in parallel for three times; and calculating calcium ion concentration represented by $\rho_{01}$, $\rho_{02}$, and $\rho_{03}$, respectively; and 6) calculation of scale inhibition rate:

a) calculating a static scale inhibition rate $\eta_1$: defining a stable calcium ion concentration of the test solution without adding the scale inhibitor as $\rho_0$; defining a stable calcium ion concentration of the test solution in the presence of the scale inhibitor as $\rho_1$; $\rho_0=(\rho_{01}+\rho_{02}+\rho_{03})/3$, $\rho_1=(\rho_{11}+\rho_{12}+\rho_{13})/3$; and calculating the static inhibition rate $\eta_1$ according to the following formula:

$$\eta_1=(\rho_1-\rho_0)/(240-\rho_0)\times 100\%$$

b) calculating a dynamic scale inhibition rate $\eta_2$: defining an average increased weight of the test piece in condition of not adding the scale inhibitor as $m_0$; defining an average increased weight of the test piece in the presence of the scale inhibitor as $m_1$; $m_0=(m_{01}'+m_{02}'+m_{03}'-m_{01}-m_{02}-m_{03})/3$, $m_1=(m_{11}'+m_{12}'+m_{13}'-m_{11}-m_{12}-m_{13})/3$; and calculating the dynamic scale inhibition rate $\eta_2$ according to the following formula:

$$\eta_2=(m_0-m_1)/m_0\times 100\%; \text{ and}$$

c) calculating a comprehensive scale inhibition rate $\eta$ according to the following formula:

$$\eta=(\eta_1+\eta_2)/2\times 100\%$$

Advantages of the invention is as follows:

1) The device for evaluating a scale inhibitor for a circulating cooling water system of the invention comprises the open vessel provided with the stirrer, the stainless steel test piece, and the condenser, thereby realizing a proper combination of a conventional static evaluation method and a dynamic evaluation method. The method of the invention is capable of reflecting the chelation, the dispersion, and the lattice distortion of the scale inhibitor, and fast evaluating the comprehensive performance of the scale inhibitor.

2) The method for evaluating a scale inhibitor of the invention has a simple operation and is timesaving. The method is capable of simulating the flow rate of the circulating cooling water, thereby providing an effective evaluating method for a development, selection, and combination of the scale inhibitors for the circulating cooling water system.

BRIEF DESCRIPTION OF THE DRAWINGS

The invention is described hereinbelow with reference to the accompanying drawings, in which.

Figure 1:
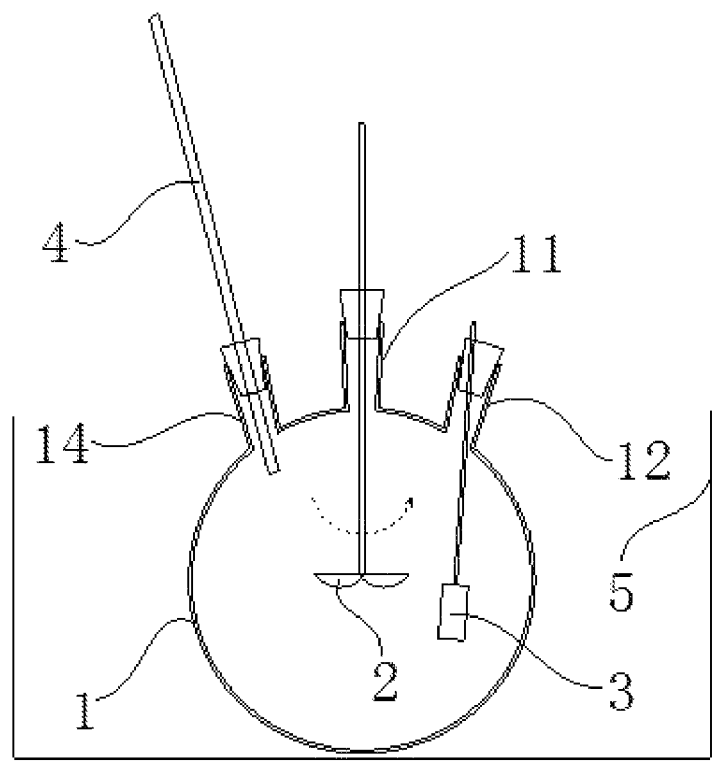
FIG. 1 is a structure diagram of a device for evaluating a scale inhibitor for a circulating cooling water system in accordance with one embodiment of the invention.

In the drawings, the following reference numbers are used: 1. Open vessel; 11. First fixing hole; 12. First test hole; 13. Second test hole; 14. Second fixing hole; 15. Third test hole; 2. Stirrer; 3. Test piece; 4. Condenser; and 5. Constant temperature heater.

DETAILED DESCRIPTION OF THE EMBODIMENTS

For further illustrating the invention, experiments detailing a device and a method for evaluating a scale inhibitor for a circulating cooling water system are described below. It should be noted that the following examples are intended to describe and not to limit the invention.

EXAMPLE 1

Figure 2:
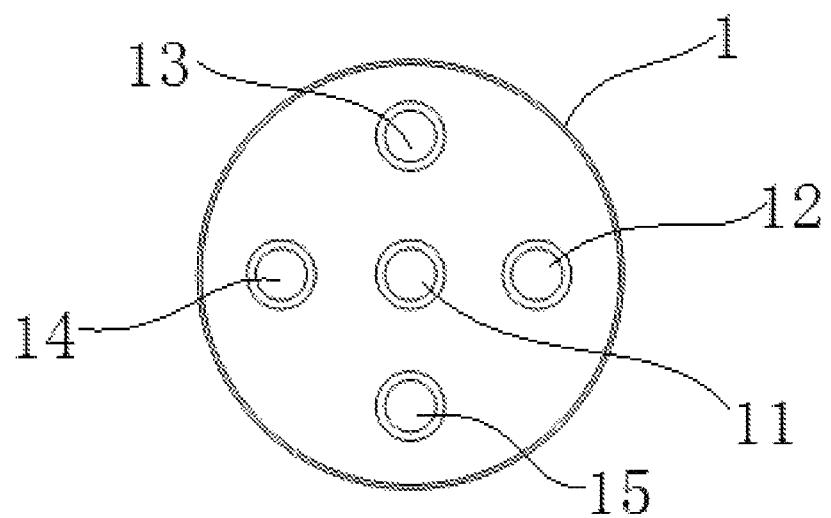
FIG. 2 is a top view of an open vessel in accordance with one embodiment of the invention.

As shown in FIGS. 1-2, a device for evaluating a scale inhibitor for a circulating cooling water system comprises: an open vessel 1; a stirrer 2; a test piece 3; a condenser 4; and a constant temperature heater 5. The open vessel 1 is disposed inside the constant temperature heater 5. The open vessel 1 is provided with a first fixing hole 11 for fixing the stirrer 2, and a second fixing hole 14 for fixing the condenser 4. The condenser 4 herein is a glass tube comprising two ends. One end of the glass tube communicates with the air inside the open vessel 1; and the other end of the glass tube communicates with the atmosphere. The glass tube has an outer diameter of 5 mm and a length of 35 cm for condensing the water vapor and maintaining a constant volume of a test solution in the open vessel 1. The open vessel 1 is provided with a first test hole 12, a second test hole 13, and a third test hole 15 for fixing test pieces 3, respectively. The test pieces herein are made of stainless steel No. 304 manufactured by Shandong Yangxin Senpu Technology Limited. The test pieces of stainless steel No. 304 have a size of 20×10×3 mm and are suspended in the test solution in the open vessel 1. An arrangement of the stainless steel test piece is in parallel with a flow direction of the test solution. The first test hole 12, the second test hole 13, the third test hole 15, and the second fixing hole 14 are evenly arranged around the first fixing hole 11.

The open vessel herein is a five-neck flask that is self-designed and is processed by Yanzhibao Experimental Equipment Marketing Center in Qinhuai district, Nanjing, China. The open vessel has a capacity of 500 mL. The first fixing hole 11, the first test hole 12, the second test hole 13, the second fixing hole 14, and the third test hole 15 are all ground according to the 24# ground standard. The first fixing hole 11 is arranged at a center position, as shown in FIG. 2.

Scale inhibition of hydrolyzed polymaleic anhydride (HPMA), provided by Nanjing Naco Water Treatment Technology Co., Ltd., was evaluated, and a method for evaluating HPMA for a circulating cooling water system comprises the following steps:

1) Treatment of a test piece:
Wash the test piece 3 in acetone in the presence of ultrasonic wave, and desiccate the test piece 3 in a desiccator.

2) Preparation of a test solution:
a) Dilute the HPMA scale inhibitor in a 100 mL volumetric flask to a HPMA concentration of 5 mg/mL (referring to a dry basis). Prepare a 0.01 mol/L EDTA standard solution and preserve the 0.01 mol/L standard EDTA solution in a brown volumetric flask. Prepare a 200 g/L potassium hydroxide solution and preserve the 200 g/L potassium hydroxide solution in a plastic open reagent bottle. Prepare a 0.01 mol/L borax buffer solution.

b) Prepare a sodium bicarbonate mother solution comprising a $HCO_3^-$ concentration of 18.3 mg/mL. Prepare a calcium chloride mother solution comprising a $Ca^{2+}$ concentration of 6.0 mg/mL. Titrate the sodium bicarbonate mother solution and the calcium chloride mother solution by using a hydrochloric acid standard solution and the EDTA standard solution, respectively. A $HCO_3^-$ concentration of the sodium bicarbonate mother solution after the titration is 18.1 mg/mL, and a $Ca^{2+}$ concentration of the calcium chloride mother solution is 5.9 mg/mL.

c) Add 300 mL distilled water into a 500 mL volumetric flask; transfer the titrated calcium chloride mother solution, 1 mL HPMA solution, 20 mL prepared borax buffer solution to the volumetric flask by using pipettes, respectively. Transfer the titrated sodium bicarbonate mother solution to the volumetric flask by using a pipette while shaking. Add distilled water into the volumetric flask to the test solution having a calcium ion concentration of 240 mg/L and a bicarbonate ion concentration of 366 mg/L;

3) Scale formation test:
Transfer the test solution prepared in step 2) to an open vessel 1; provide three test pieces 3 prepared in step 1) and measure weight thereof represented by $m_{11}$, $m_{12}$, and $m_{13}$, respectively, as shown in Table 1.

TABLE 1

Test data and calculating results of Examples 1-3

|  | HPMA | HEDP | PAA |
| --- | --- | --- | --- |
| $m_{01}$ (mg) | 4262.6 | 4262.6 | 4262.6 |
| $m_{02}$ (mg) | 3994.2 | 3994.2 | 3994.2 |
| $m_{03}$ (mg) | 4255.3 | 4255.3 | 4255.3 |
| $m_{01}'$ (mg) | 4266.0 | 4266.0 | 4266.0 |
| $m_{02}'$ (mg) | 3997.2 | 3997.2 | 3997.2 |

TABLE 1-continued

Test data and calculating results of Examples 1-3

|  | HPMA | HEDP | PAA |
| --- | --- | --- | --- |
| $m_{03}'$ (mg) | 4258.5 | 4258.5 | 4258.5 |
| $m_0$ (mg) | 3.2 | 3.2 | 3.2 |
| $m_{11}$ (mg) | 4209.9 | 4309.9 | 4109.5 |
| $m_{12}$ (mg) | 4033.1 | 4233.2 | 4333.1 |
| $m_{13}$ (mg) | 4309.8 | 4109.8 | 4009.8 |
| $m_{11}'$ (mg) | 4211.8 | 4311.8 | 4111.8 |
| $m_{12}'$ (mg) | 4035.2 | 4235.0 | 4335.6 |
| $m_{13}'$ (mg) | 4311.8 | 4111.6 | 4011.9 |
| $m_1$ (mg) | 2.0 | 1.8 | 2.3 |
| $\rho_{01}$ (mg/L) | 108.5 | 108.5 | 108.5 |
| $\rho_{02}$ (mg/L) | 108.7 | 108.7 | 108.7 |
| $\rho_{03}$ (mg/L) | 107.4 | 107.4 | 107.4 |
| $\rho_0$ (mg/L) | 108.2 | 108.2 | 108.2 |
| $\rho_{11}$ (mg/L) | 215.4 | 223.8 | 211.4 |
| $\rho_{12}$ (mg/L) | 215.8 | 224.1 | 210.7 |
| $\rho_{13}$ (mg/L) | 213.5 | 222.1 | 209.1 |
| $\rho_1$ (mg/L) | 214.9 | 223.3 | 210.4 |
| static scale inhibition rate $\eta_1$ (%) | 81.0 | 87.3 | 77.5 |
| dynamic scale inhibition rate $\eta_2$ (%) | 37.5 | 43.8 | 28.1 |
| comprehensive scale inhibition rate $\eta$ (%) | 59.3 | 65.6 | 52.8 |

Fix the three test pieces 3 in a first test hole 12, a second test hole 13, and a third test hole 15 by using stainless steel strips, respectively, for suspending the three test pieces 3 in the test solution. Fix a condenser 4 in a second fixing hole 14; fix a stirrer 2 in a first fixing hole 11, control a stirrer speed at 160 rpm; maintain the open vessel 1 inside a constant temperature heater 5 for 10 h; and take off the three test pieces 3, desiccate, and measure weight thereof represented by $m_{11}'$, $m_{12}'$, $m_{13}'$, respectively, as shown in Table 1. The constant temperature heater 5 herein is a constant temperature water bath, and a temperature thereof is controlled at 80° C.

4) Measurement of calcium ion concentration:
Cool the test solution in the open vessel 1 to a room temperature; transfer the test solution and filter the test solution by using a middle speed quantitative filter paper; and add 25 mL of a filtrate to a 250 mL Erlenmeyer flask. Add 55 mL of distilled water, 5 mL of the potassium hydroxide solution prepared in step 2), and 0.1 g of calconcarboxylic acid into the Erlenmeyer flask to yield a mixture. Titrate the mixture in parallel for three times by using the EDTA standard solution obtained in step 2). Calculate calcium ion concentration represented by $\rho_{11}$, $\rho_{12}$, and $\rho_{13}$, respectively, as shown in Table 1.

5) Blank test:
Repeat steps 1)-4) to conduct the blank test in which prepare a test solution without adding the scale inhibitor; measure weight of three test pieces 3 before the blank test represented by $m_{01}$, $m_{02}$, and $m_{03}$; measure weight of the three test pieces 3 after the blank test represented by $m_{01}'$, $m_{02}'$, and $m_{03}'$; titrate calcium ion concentration of the test solution in parallel for three times; and calculate calcium ion concentration represented by $\rho_{01}$, $\rho_{02}$, and $\rho_{03}$, respectively.

6) Calculation of scale inhibition rate:
a) Calculate a static scale inhibition rate $\eta_1$: define a stable calcium ion concentration of the test solution without adding the scale inhibitor as $\rho_0$; define a stable calcium ion concentration of the test solution in the presence of the scale inhibitor as $\rho_1$: $\rho_0=(\rho_{01}+\rho_{02}+\rho_{03})/3=108.2$ mg/L, $\rho_1=(\rho_{11}+\rho_{12}+\rho_{13})/3=214.9$ mg/L; and calculate the static inhibition rate $\eta_1$ according to the following formula:

$$\eta_1=(\rho_1-\rho_0)/(240-\rho_0)\times 100\%=81.0\%$$

b) Calculate a dynamic scale inhibition rate $\eta_2$: define an average increased weight of the test piece 3 in condition of not adding the scale inhibitor as $m_0$; define an average increased weight of the test piece 3 in the presence of the scale inhibitor as $m_1$; $m_0=(m_{01}'+m_{02}'+m_{03}'-m_{01}-m_{02}-m_{03})/3=3.2$ mg, $m_1=(m_{11}'+m_{12}'+m_{13}'-m_{11}-m_{12}-m_{13})/3=2.0$ mg; and calculate the dynamic scale inhibition rate $\eta_2$ according to the following formula:

$$\eta_2=(m_0-m_1)/m_0\times100\%=37.5\%; \text{ and}$$

c) Calculate a comprehensive scale inhibition rate $\eta$ according to the following formula:

$$\eta=(\eta_1+\eta_2)/2\times100\%=59.3\%$$

EXAMPLE 2

In this example, the performance of scale inhibition of 1-hydroxyethylidene-1, 1-diphosphonic acid (HEDP), provided by Nanjing Naco Water Treatment Technology Co., Ltd., was evaluated. A device and a method for evaluating HEDP for a circulating cooling water system are the same as those of Example 1, and test data and calculating results are shown in Table 1.

EXAMPLE 3

In this example, the performance of scale inhibition of polyacrylic acid (PAA), provided by Nanjing Naco Water Treatment Technology Co., Ltd., was evaluated. A device and a method for evaluating PAA for a circulating cooling water system are the same as those of Example 1, and test data and calculating results are shown in Table 1.

The device and the method for evaluating a scale inhibitor for a circulating cooling water system of the invention realizes a proper combination of a conventional static evaluation method and a dynamic evaluation method. The method of the invention is capable of reflecting the chelation, the dispersion, and the lattice distortion of the scale inhibitor, and fast evaluating the comprehensive performance of the scale inhibitor. The method of the invention has a simple operation and is timesaving, thereby providing an effective evaluating method for the development, selection, and combination of the scale inhibitors for the circulating cooling water system.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for evaluating a scale inhibitor, the device comprising:
   a) an open vessel (1), the open vessel (1) is adapted to contain a test solution having calcium ions; and the open vessel (1) comprising a first fixing hole (11), a second fixing hole (14), and at least one test hole;
   b) a stirrer (2), the stirrer (2) comprising a rotational shaft and a blade;
   c) a stainless-steel piece (3);
   d) a condenser (4); and
   e) a constant temperature heater (5);
   wherein:
   the open vessel (1) is operatively disposed inside the constant temperature heater (5);
   the stirrer (2), the stainless-steel piece (3), and the condenser (4) are operatively inserted into the open vessel (1) through the first fixing hole (11), the test hole, and the second fixing hole (14), respectively;
   the stirrer (2) is operatively fixed by the first fixing hole (11);
   the condenser (4) is operatively fixed by the second fixing hole (14);
   the stainless-steel piece (3) is operatively fixed by the test hole;
   the constant temperature heater (5) is adapted to heat the open vessel (1) at a constant temperature;
   the condenser (4) is adapted to condense water vapor formed by evaporation of the test solution, thereby maintaining a volume of the test solution constant;
   the blade is operatively inserted into the test solution, and is adapted to stir the test solution;
   the stainless-steel piece (3) is operatively inserted into the test solution, and is adapted to absorb calcium carbonate formed by crystallization of the calcium ions; and
   the stainless-steel piece (3) is operatively disposed parallel to the rotational shaft.

2. The device of claim 1, wherein:
   the open vessel (1) comprises three test holes; and
   the three test holes and the second fixing hole (14) are evenly arranged around the first fixing hole (11).

3. The device of claim 1, wherein
   the condenser (4) is a glass tube comprising two ends;
   one end of the glass tube communicates with the air inside the open vessel (1);
   the other end of the glass tube communicates with the atmosphere;
   the glass tube has an outer diameter between 3 and 6 mm and a length between 30 and 40 cm for condensing water vapor.

4. The device of claim 2, wherein
   the condenser (4) is a glass tube comprising two ends;
   one end of the glass tube communicates with the air inside the open vessel (1);
   the other end of the glass tube communicates with the atmosphere;
   the glass tube has an outer diameter between 3 and 6 mm and a length between 30 and 40 cm for condensing water vapor.

* * * * *